(12) United States Patent
Lim

(10) Patent No.: US 8,123,070 B2
(45) Date of Patent: Feb. 28, 2012

(54) STORAGE COVER FOR STORAGE CASE

(76) Inventor: Heung Ho Lim, Seoul (KR)

( * ) Notice: Subject to any disclaimer, the term of this patent is extended or adjusted under 35 U.S.C. 154(b) by 449 days.

(21) Appl. No.: 11/997,320

(22) PCT Filed: Sep. 5, 2007

(86) PCT No.: PCT/KR2007/004285
§ 371 (c)(1),
(2), (4) Date: Jan. 29, 2008

(87) PCT Pub. No.: WO2008/030037
PCT Pub. Date: Mar. 13, 2008

(65) Prior Publication Data
US 2010/0089934 A1    Apr. 15, 2010

(51) Int. Cl.
*B65D 43/04* (2006.01)
(52) U.S. Cl. .............. 220/806; 220/796; 220/367.1
(58) Field of Classification Search .......... 220/359.3, 220/796, 797, 805, 780, 782, 806, 367.1; 215/260; 426/118
See application file for complete search history.

(56) References Cited

U.S. PATENT DOCUMENTS
5,762,228 A * 6/1998 Morgan et al. ............ 220/367.1
(Continued)

FOREIGN PATENT DOCUMENTS
JP    3065300 U    10/1999
(Continued)

*Primary Examiner* — Anthony Stashick
*Assistant Examiner* — Kareen Rush
(74) *Attorney, Agent, or Firm* — John K. Park; Park Law Firm (57) ABSTRACT

A storage cover for a storage case is provided. The storage cover for the storage case for opening and closing an opening formed on one side of a storage case to take in and out stored goods includes a plate-shaped cover unit for covering the upper part of the opening and a flexible rim extended along the edge of the cover unit in the direction of the thickness of the cover unit, made of an elastic material to be elastically extended, and pulled back toward the upper part of the cover unit when the opening is opened and pulled back toward the lower part of the cover unit when the opening is closed to surround the external circumference of the opening. Therefore, opening and closing operations are simply performed so that the storage cover can be conveniently used and that airtight coupling force can be maintained in spite of the repeated opening and closing operations.

15 Claims, 8 Drawing Sheets

U.S. PATENT DOCUMENTS

| | | | | |
|---|---|---|---|---|
| 5,944,211 | A * | 8/1999 | Woodnorth et al. | 220/203.13 |
| 6,010,027 | A * | 1/2000 | Fujii et al. | 220/592.2 |
| 6,182,850 | B1 * | 2/2001 | Marbler et al. | 220/359.3 |
| 2003/0019878 | A1 * | 1/2003 | Scarabelli et al. | 220/796 |
| 2004/0206765 | A1 * | 10/2004 | McMahon et al. | 220/780 |

FOREIGN PATENT DOCUMENTS

| | | |
|---|---|---|
| KR | 20-2005-0029895 | 1/2006 |
| KR | 10-2005-0032716 | 6/2006 |
| KR | 20-2006-0022862 | 12/2006 |

* cited by examiner

STORAGE COVER FOR STORAGE CASE

TECHNICAL FIELD

The present invention relates to a storage cover for a storage case, and more particularly to, a storage cover for a storage case capable of being easily used by pulling back upper and lower parts to simply perform opening and closing operations and of maintaining airtight coupling force in spite of the repeated opening and closing operations.

BACKGROUND ART

In general, a storage case for keeping stored goods (for example, food) and a storage cover for opening and closing the opening of the storage case are airtightly coupled with each other to keep the stored goods contained in the storage case for a long time or to maintain the freshness of the stored goods.

Recently, various technologies of improving airtightness between the storage cover and the storage case when the storage cover and the storage case are coupled with each other are applied.

For example, like in the lock and lock (the name of a product), a technology of airtightly coupling the storage cover and the storage case with each other so that the airtightness between the storage cover and the storage case is maintained to keep the stored goods is applied.

In the case of the lock and lock and similar products, locking units for coupling the storage case and the storage cover with each other are provided.

The locking units are foldably provided on the sides of the storage cover and are coupled with and released from the coupling protrusions formed on the external rim of the storage case.

However, in the storage case and the storage cover that are coupled with and released from each other by the locking units, since the opening and closing operations of the storage cover coupled with and released from the storage case by operating the locking units (for example, the storage case is held by one hand and the storage cover is held by the other hand to perform opening and closing operations or, after one side of the storage cover is coupled with and released from the storage case, the same operation is repeated for several times in different parts to perform the opening and closing operations) are very complicated, it is inconvenient to use the storage case and the storage cover.

In addition, since the locking units integrated with the storage cover to be folded are torn by the folding operation repeated for several times or the gap between the storage case and the storage cover improves when the storage case and the storage cover are used for a long time, the airtightness between the storage case and the storage cover remarkably deteriorates in comparison with initial airtightness.

Furthermore, since the storage cover made of flexible rubber or synthetic resin is thin, the storage cover is easily transformed and twisted.

In addition, since the storage cover is vulnerable to heat (for example, the storage cover is transformed when the heat of no less than 50㎝ is applied), it is not possible to heat the storage case and the storage cover to sterilize the storage case and the storage cover.

DISCLOSURE

Technical Problem

Therefore, the present invention has been made in view of the above problems, and it is an object of the present invention to provide a storage cover for a storage case capable of being easily used by pulling back upper and lower parts to simply perform opening and closing operations and of maintaining airtight coupling force in spite of the repeated opening and closing operations.

It is another object of the present invention to provide a storage cover for a storage case that is prevented from being transformed and twisted by a reinforcing unit when the storage cover is made of flexible rubber or synthetic resin.

Technical Solution

In order to accomplish the above and other objects, there is provided a storage cover 100 for a storage case 200 for opening and closing an opening 210 formed on one side of a storage case 200 to take in and out stored goods. The storage cover 100 for the storage case 200 includes a plate-shaped cover unit 110 for covering the upper part of the opening 210 and a flexible rim 140 extended along the edge of the cover unit 110 in the direction of the thickness of the cover unit 110, made of an elastic material to be elastically extended, and pulled back toward the upper part of the cover unit 110 when the opening 210 is opened and pulled back toward the lower part of the cover unit 110 when the opening 210 is closed to surround the external circumference of the opening 210.

The cover unit 110 further includes a plurality of settling protrusions 111 that protrude toward the storage case 200. The settling protrusions 111 can be separated from the flexible rim 140 by no less than the thickness t1 of the side walls of the storage case 200 to guide the cover unit 110 so that the cover unit 110 is settled in the correct position of the opening 210. Here, the plurality of settling protrusions 111 can be connected to each other to be ring-shaped.

At least one airtight protrusions 142a that protrude toward the side walls 214 of the storage case 200 to be connected to the side walls 214 to Improve airtightness can be further formed in at least one of the settling protrusions 111 and the flexible rim 140.

Here, the airtight protrusions 142a can be provided as wrinkled airtight protrusions 142b, as the wrinkled airtight protrusions 142b and protrusion-shed airtight protrusions 142c, or protrusion-shaped airtight protrusions 142d.

Airtight protrusions 142e are protrusion-shaped and at least one airtight protrusions 142e can be selectively provided on both sides of the flexible rim 140 to correspond to both surfaces of the cover unit 110. The flexible rim 140 can be made of silicon having elasticity.

In addition, the cover unit 110 and the flexible rim 140 are made of silicon having elasticity and reinforcing units 120 that let the cover unit 110 maintain the original shape when the flexible rim 140 is pulled back can be further provided in the cover unit 110.

The reinforcing units 120 can include reinforcing rings 121 adjacent to the edge of the cover unit 110 to be buried in the cover unit 110.

The reinforcing units 120 can be provided to protrude toward the storage case 200 and can be separated from the flexible rim 140 by no less than the thickness of the side walls of the storage case 200 to guide the cover unit 110 so that the cover unit 110 is settled in the correct position of the opening 210.

At least one airtight protrusions 142a and 142f that protrude toward the side walls 214 of the storage case 200 to be connected to the side walls 214 to improve airtightness can be formed in at least one of the reinforcing units 120 and the flexible rim 140.

Airtight protrusion accommodating units 212 in which the airtight protrusions 142c are accommodated and from which the airtight protrusions 212 are released are provided on the side walls 214 so that the airtight protrusions 142c are inserted into the airtight protrusion accommodating units 212 when the opening 210 is closed to prevent the storage case 200 from being deviated from the storage cover 100.

The airtight protrusions 142a can be wrinkled.

The cover unit 110 can further include at least one ventilation units 150 for introducing and discharging the air to the inside and outside of the storage case 200 when the opening 210 is closed.

The ventilation unit 150 can include a ventilation hole 152 opened when external force is applied to discharge the air in the storage case 200 to the outside and closed when external force is removed to prevent the air from being introduced to the storage case 200.

The flexible rim 140 can be provided to have a thickness no less than the thickness of a strap hinge 130 connected to the cover unit 110.

DESCRIPTION OF DRAWINGS

The above and other objects, features and other advantages of the present invention will be more clearly understood from the following detailed description taken in conjunction with the accompanying drawings, in which.

BEST MODE

Figure 1:
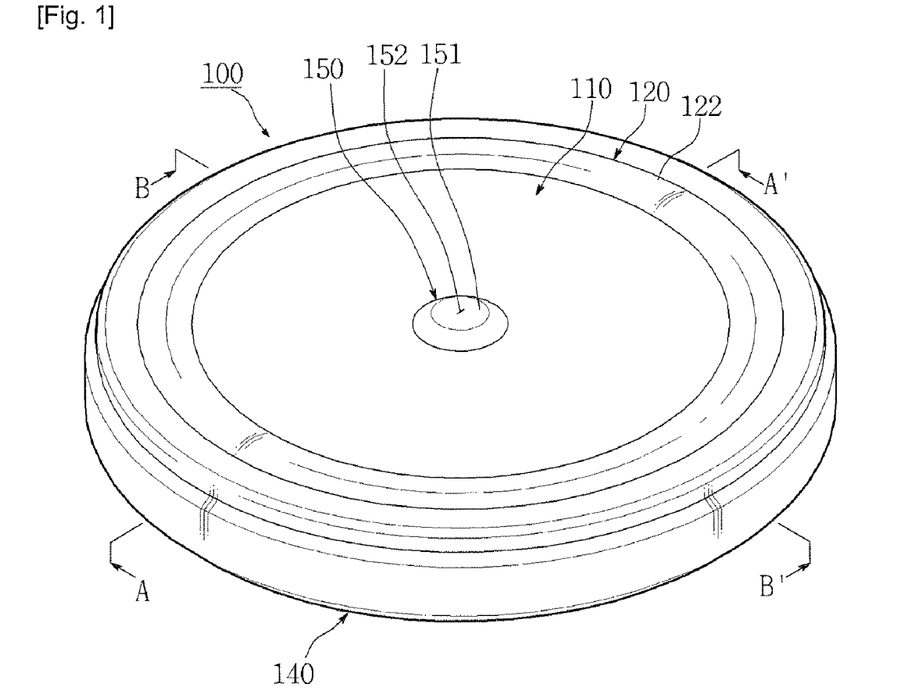
FIG. 1 is a perspective view illustrating a storage cover according to an embodiment of the present invention.

FIG. 1 is a perspective view illustrating a storage cover according to an embodiment of the present invention.

Referring to FIG. 1, a storage cover 100 for a storage case 200 (refer to FIG. 9) according to an embodiment of the present invention for opening and closing an opening part 210 that is formed on one side of the storage case 200 and through which stored goods are taken in and out includes a plate-shaped cover unit 110 for covering the upper part of the opening 210 and a flexible rim 140 extended along the edge of the cover unit 110 in the direction of the thickness of the cover unit 110, made of an elastic material to be elastically extended, and pulled back toward the upper part of the cover unit 110 when the opening 210 is opened and pulled back toward the lower part of the cover unit 110 when the opening 210 is closed to surround the external circumference of the opening 210.

Here, the storage case 200 is used to keep (for example, the stored goods are taken in the storage case and are kept in a refrigerator, indoors, and outdoors) the stored goods (for example, food).

The opening 210 for taking in and out the stored goods is provided on one side of the storage case 200.

Figure 15:
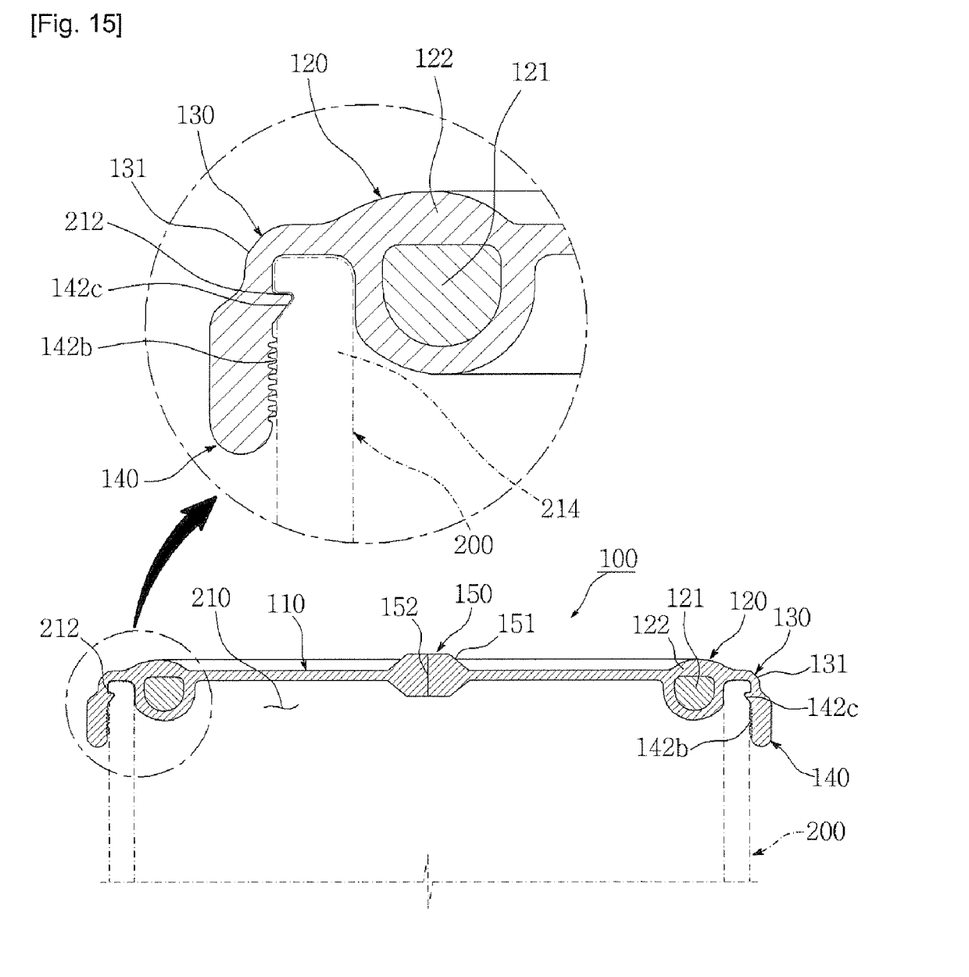
FIG. 15 is a sectional view illustrating the storage cover according to still another embodiment of the present invention.

As illustrated in FIG. 15, airtight protrusion accommodating units 212 for coupling the storage cover 100 can be provided on the side walls 214 of the storage case 200.

Figure 2:
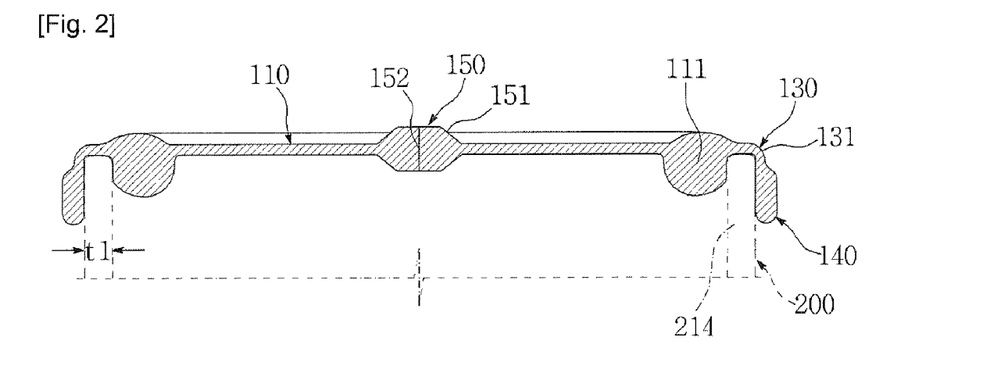
FIG. 2 is a sectional view illustrating the storage cover provided with a cover unit made of a hard material according to an embodiment of the present invention.

FIG. 2 is a sectional view illustrating the storage cover 100 provided with the cover unit 110 made of a hard material according to an embodiment of the present invention.

Referring to FIG. 2, the storage cover 100 is formed on one side of the storage case 200 to open and close the opening 210 through which the stored goods are taken in and out.

The storage cover 100 can include the cover unit 110 for covering the upper part of the opening 210 and the flexible rim 140 pulled back toward the upper part and the lower part of the cover unit 110 to open and close the opening 210.

Here, the cover unit 110 can have various shapes. For example, when the storage case 200 is square box-shaped or cylindrical, the cover unit 110 can be square or circular to correspond to the opening 210 of the storage case 200.

The cover unit 110 can be made of various materials. For example, in addition to the flexible rim 140, the cover unit 110 can be made of a hard material or a flexible material (for example, silicon) like the flexible rim.

When the cover unit 110 is made of a hard material, the thickness of the cover unit 110 can be 1 mm to 3 mm and can be preferably 2 mm so that the original shape of the cover unit 110 is maintained or that a user has a proper sense of gripping.

As illustrated in FIG. 2, settling protrusions 111 that protrude toward the storage case 200 to guide the cover unit 110 so that the cover unit 110 is settled in the correct position of the opening 210 when the storage cover 100 is coupled with the storage case 200 can be provided in the cover unit 110.

The settling protrusions 111 are preferably separated from the flexible rim 140 by no less than the thickness (refer to t1 of FIG. 2) of the side walls of the storage case 200 so that the side walls 214 of the storage case 200 are easily coupled.

The settling protrusions 111 can have various shapes such as square protrusions or cylindrical protrusions.

The settling protrusions 111 can be connected to each other to be ring-shaped or can be separated from each other.

The settling protrusions 111 can be molded to be integrated with the cover unit 110 made of a hard material or can be separately formed to be attached to the cover unit 110.

Figure 5:
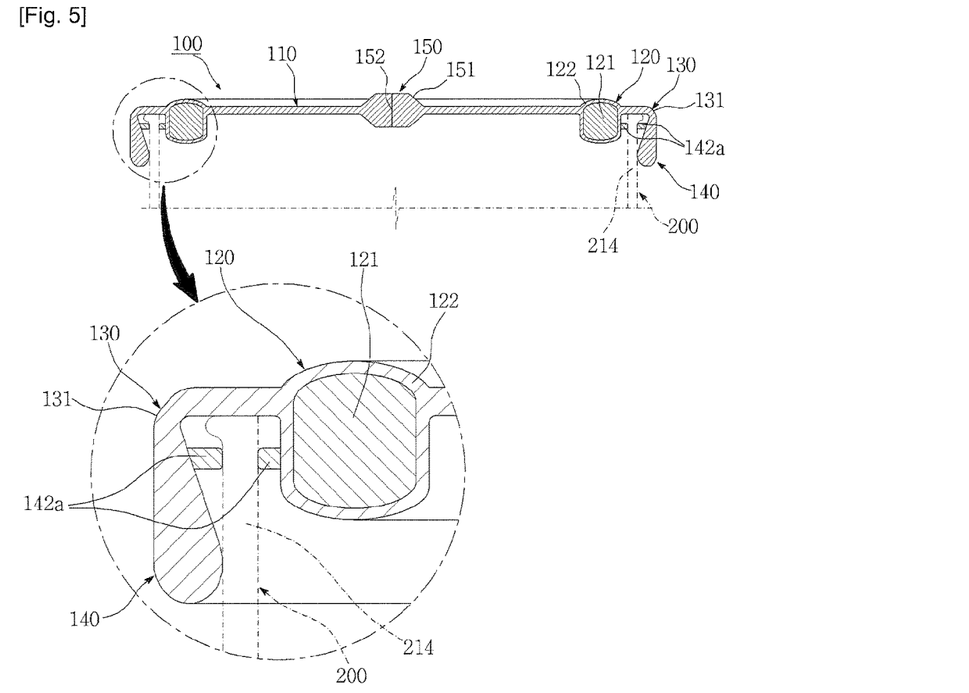
FIG. 5 is a sectional view illustrating a storage cover provided with a reinforcing unit according to another embodiment of the present invention.

As illustrated in FIG. 5, at least one airtight protrusions 142a that protrude toward the side walls 214 of the storage case 200 to be connected to the side walls 214 to improve airtightness can be provided in the settling protrusions 111.

Figure 6:
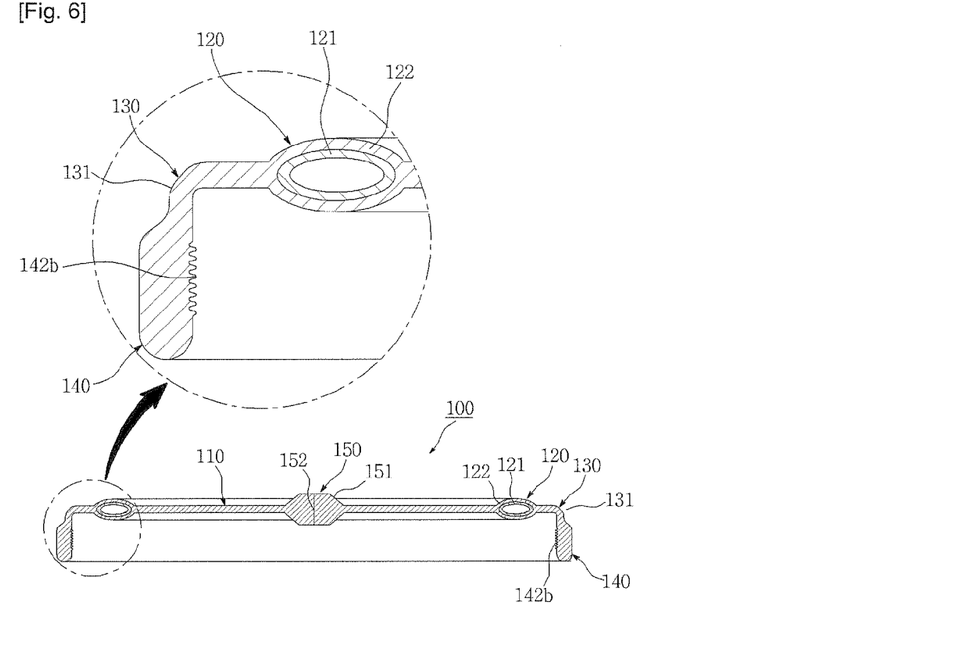
FIG. 6 is a sectional view illustrating airtight protrusions and a reinforcing ring according to an embodiment of the present invention.
Figure 7:
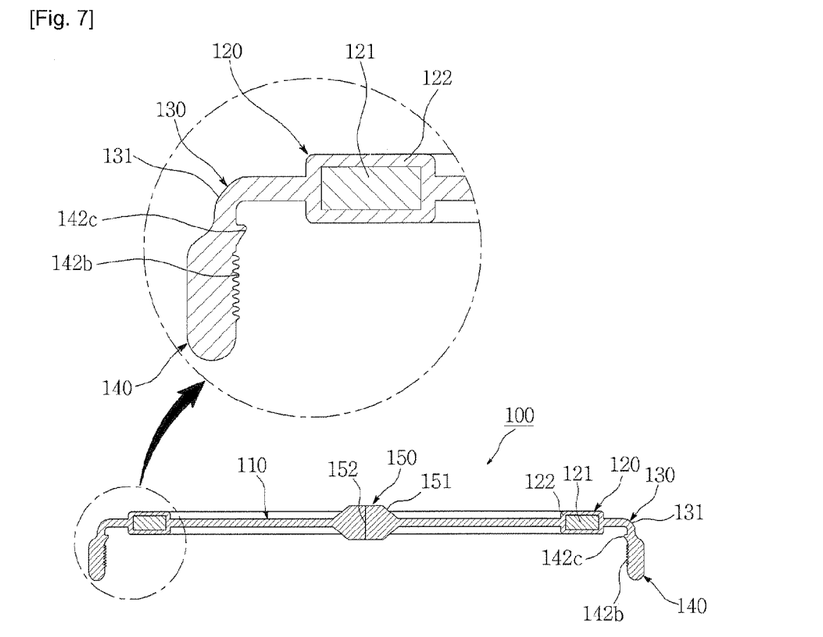
FIG. 7 is a sectional view illustrating airtight protrusions and a reinforcing ring according to another embodiment of the present invention.
Figure 8:
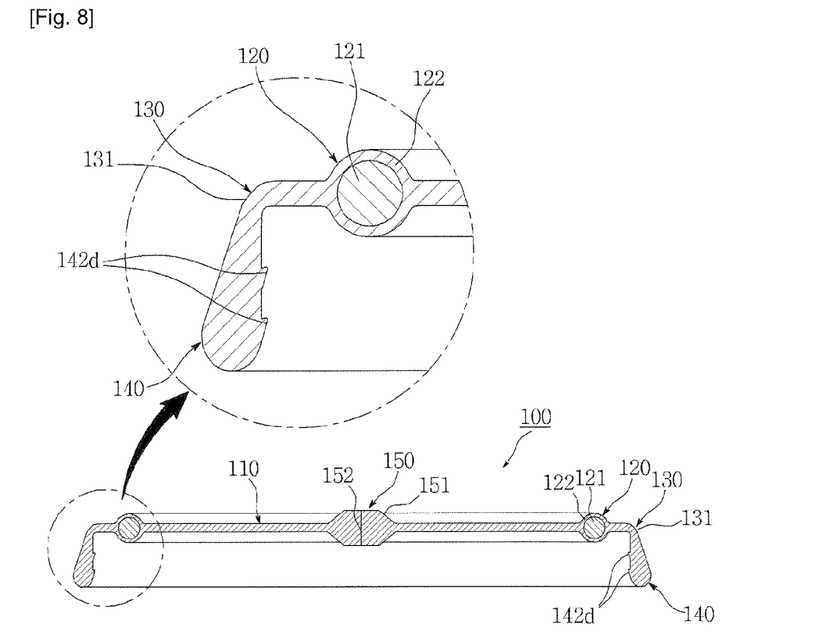
FIG. 8 is a sectional view illustrating airtight protrusions and a reinforcing ring according to still another embodiment of the present invention.

The airtight protrusions 142a can have various shapes. For example, as illustrated in FIG. 6, wrinkled airtight protrusions 142b can be provided, as illustrated in FIG. 7, the wrinkled airtight protrusions 142b and protrusion-shaped airtight protrusions 142c can be provided together, or, as illustrated in FIG. 8, protrusion-shaped airtight protrusions 142d can be additionally provided.

When the wrinkled airtight protrusions 142b are provided, the wrinkled parts are smoothed out in connection with the external circumferences of the side walls 214 of the storage case 200 to improve elasticity and the airtightness.

When the protrusion-shaped airtight protrusions 142c are provided, as illustrated in FIG. 15, the airtight protrusions 142c can correspond to the airtight protrusion accommodating units 212 provided on the side walls of the storage case 200.

In this case, the airtight protrusions 142c are inserted into the airtight protrusion accommodating units 212 when the storage case 200 and the storage cover 100 are coupled with each other to prevent the storage case 200 from deviating from the storage cover 110 when the opening 210 is closed.

The airtight protrusions 142a, 142b, 142c, and 142d are airtightly attached to the internal and external circumferences of the side walls 214 of the storage case 200 to prevent the stored goods from leaking to the gap that can be generated between the storage case 200 and the storage cover 100 that are coupled with each other when the storage case 200 is inclined or shaken or external shock is generated.

The airtight protrusions 142a, 142b, 142c, and 142d can be band-shaped to be connected to the flexible rim 140 or can be separated from the flexible rim 140.

Figure 14:
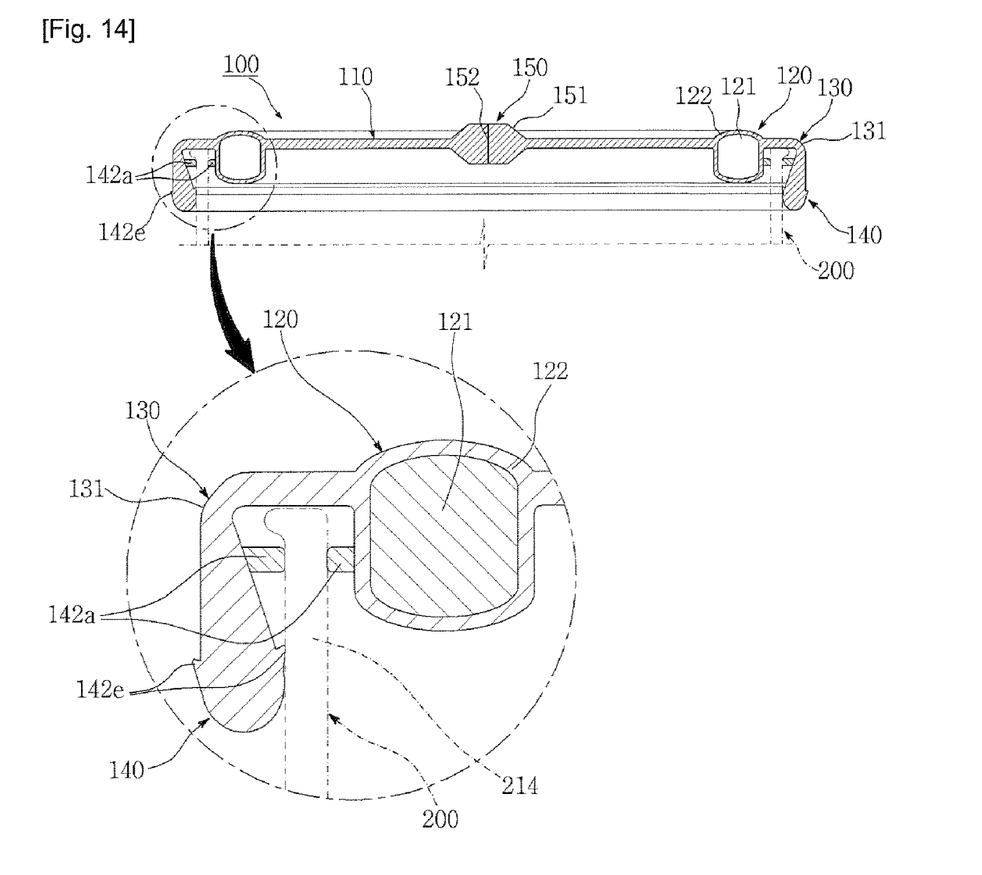
FIG. 14 is a sectional view illustrating the storage cover according to another embodiment of the present invention.

Airtight protrusions 142e are protrusion-shaped and, as illustrated in FIG. 14, at least one airtight protrusions 142e can be selectively provided on both sides of the flexible rim 140 to correspond to both surfaces of the cover unit 110.

Figure 3:
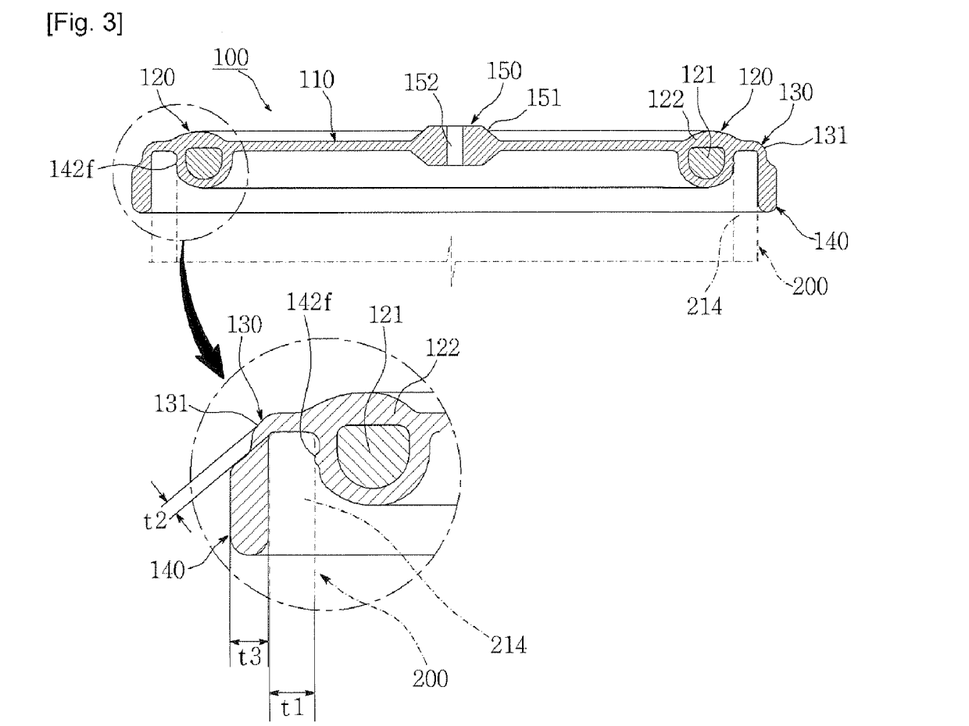
FIG. 3 is a sectional view taken along the line A-A' of FIG. 1.
Figure 4:
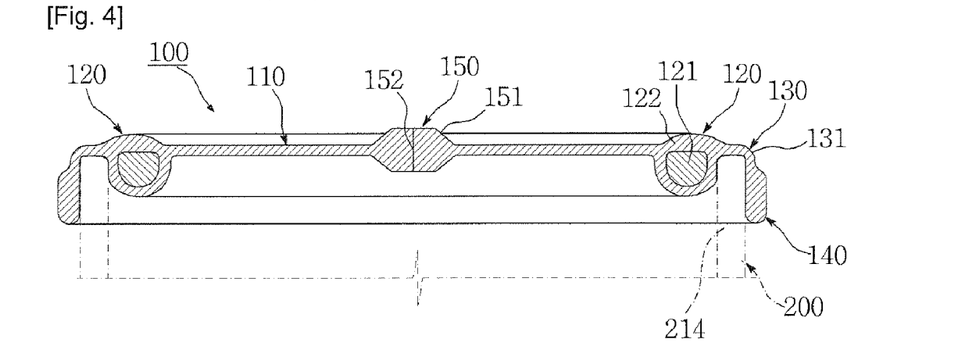
FIG. 4 is a sectional view taken along the line B-B' of FIG. 1.

As illustrated in FIGS. 3 and 4, a ventilation unit 150 is provided in the cover unit 110 to introduce and discharge the air to the inside and the outside of the storage case 200 when the opening 210 is closed.

The ventilation unit 150 can include protrusion jaws 151 formed to protrude above the upper and lower surfaces in the center of the cover unit 110 and a ventilation hole 152 provided to penetrate the protrusion jaws 151.

Here, the protrusion jaws 151 can be provided so that the upper and lower widths of both ends are reduced in the center.

The ventilation hole 152 can have various shapes. For example, as illustrated in FIGS. 3 and 4 taken along the lines A-A'? and B-B' the ventilation hole 152 can be provided to correspond to the section of a straight screwdriver.

When the cover unit 110 is made of a flexible material, as illustrated in FIG. 3, reinforcing units 120 are provided in the cover unit 110 so that the original shape of the cover unit 110 is maintained when the flexible rim 140 is pulled back.

When the cover unit 110 is made of a hard material, the thickness of the cover unit 110 can be 1 mm to 3 mm and can be preferably 2 mm so that the cover unit 110 is prevented from being torn or that a user has a proper sense of gripping.

Since the reinforcing units 120 can have the same function as the above-described settling protrusions 111, the reinforcing units 120 are separated from the flexible rim 140 by no less than the thickness (refer to t1 of FIG. 3) of the side walls of the storage case 200 and protrude toward the storage case 200 by no less than a predetermined length.

The reinforcing units 120 prevent the cover unit 110 from being pulled back in the position where reinforcing rings 121 are provided when the flexible rim 140 is pulled back toward the upper and lower parts to prevent the cover unit 110 from being transformed (for example, to prevent the cover unit 110 from being concavely folded).

At least one airtight protrusions 142a and 142f that protrude toward the side walls 214 of the storage case 200 to be connected to the side walls 214 to improve the airtightness can be provided in the reinforcing units 120. The airtight protrusions 142a and 142f can have various shapes such as protrusions or wrinkles.

The airtight protrusions 142a and 142f have the same function as the above-described airtight protrusions 142b, 142c, 142d, and 142e.

The reinforcing units 120 include the reinforcing rings 121 adjacent to the edge of the cover unit 110 to be buried and protecting plates 122 for surrounding the reinforcing rings 121 to protect the reinforcing rings 121. Here, the reinforcing rings 121 can have various shapes. For example, as illustrated in FIG. 6, the reinforcing rings 121 can be pipe-shaped so that the section of each of the reinforcing rings 121 has a space in the center or, as illustrated in FIGS. 7 and 8, the reinforcing rings 121 can be rod-shaped. In this case, the section of each of the reinforcing rings 121 can be square or circular. However, the shape of the section of each of the reinforcing rings 121 is not limited to the above.

The reinforcing rings 121 can be made of various materials such as metal or synthetic resin having large hardness.

The reinforcing rings 121 can be made of the same material as the cover unit 110 or can be made of a different material from the cover unit 110.

The flexible rim 140 is extended in the direction of the thickness of the cover unit 110, is made of an elastic material to be elastically extended, and is pulled back toward the upper part of the cover unit 110 when the opening 210 is opened and pulled back toward the lower part of the cover unit 110 when the opening 210 is closed to surround the external circumference of the opening 210.

The flexible rim 140 can have various shapes. For example, as illustrated in FIG. 2, the flexible rim 140 is provided so that one surface connected to the external circumferences of the side walls 214 is flat (for example, the flexible rim 140 is straight), as illustrated in FIG. 3, the flexible rim 140 is provided to have the same thickness (refer to t3 of FIG. 3) in a predetermined area, or, as illustrated in FIG. 5, the flexible rim 140 is provided to become thick from the cover unit 110 (for example, the end is club-shaped).

The flexible rim 140 can have various thicknesses. The thickness of the flexible rim 140 is preferably no less than the thickness (refer to t2 of FIG. 3) of a strap hinge 130 connected to the cover unit 110.

For example, the thickness of the center of the flexible rim 140 can be 3.5 mm to 5 mm and is preferably 4.2 mm so that coupling force is optimized when the flexible rim 140 is connected to the external circumference of the storage case 200.

In this case, when the flexible rim 140 is pulled back toward the upper and lower parts, folding is concentrated on the strap hinge 130 and airtightness improves when the storage case 200 and the storage cover 100 are coupled with each other.

Since the flexible rim 140 shrank inside due to the characteristic of an elastic material, the flexible rim 140 can maintain a smaller diameter than the external diameter of the cover unit 110.

Figure 9:
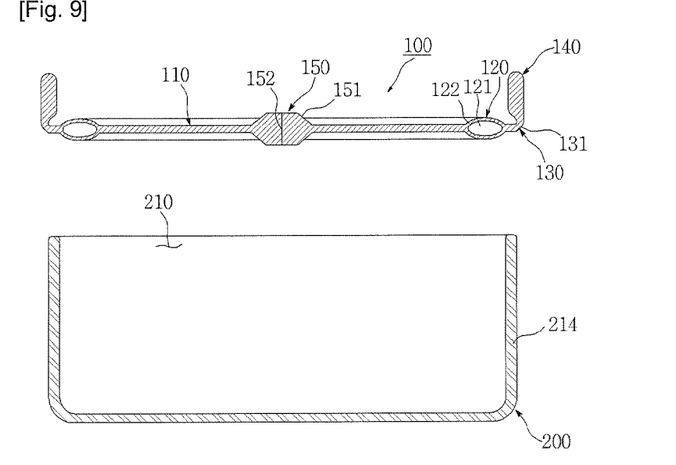
FIG. 9 is a sectional view illustrating a state before the storage case and the storage cover according to an embodiment of the present invention are coupled with each other.

The flexible rim 140 can be used in a state of being pulled back on one side regardless of the upper and lower sides based on the cover unit 110. As illustrated in FIG. 9, the flexible rim 140 is elastically extended and maintains the state of being pulled back to the opposite side of the storage case 200 when the flexible rim 140 is released from the storage case 200 in order to take the stored goods in the storage case 200 or to take out the stored goods from the storage case 200.

Figure 10:
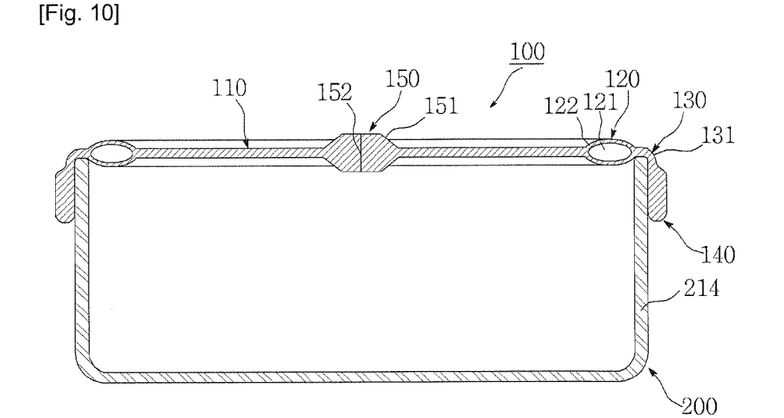
FIG. 10 is a sectional view illustrating a state where the storage case and the storage cover of FIG. 9 are coupled with each other.

As illustrated in FIG. 10, the flexible rim 140 is elastically extended and is pulled back toward the storage case 200 to surround the external circumference of the opening 210 when the flexible rim 140 is coupled with the storage case 200 in a state where the stored goods are taken in the storage case 200 or the stored goods are taken out from the storage case 200.

The flexible rim 140 is connected to the external circumferences of the side walls 214 of the storage case 200 so that at least one airtight protrusions 142a, 142b, 142c, 142d, and 142e that improve the airtightness can be provided.

The airtight protrusions 142a, 142b, 142c, 142d, and 142e perform the same function as the above-described airtight protrusions.

The strap hinge 130 is provided to connect the cover unit 110 and the flexible rim 140 to each other so that the cover unit 110 and the flexible rim 140 are integrated with each other.

The strap hinge 130 is formed on the circumference of the cover unit 110 so that the external surface of the strap hinge 130 has an inclined surface 131.

The inclined surface 131 of the strap hinge 130 can be provided to have a downward inclined angle of 40° to 50°. The downward inclination angle is preferably 45° in order to prevent the thickness of the strap hinge 130 from being reduced so that the life is reduced when the angle of the inclined surface 131 is smaller than 40° or to prevent the thickness of the strap hinge 130 from increasing so that excessive force is applied when the flexible rim 140 is pulled back toward the upper part of the cover unit 110 in a case where the angle of the inclined surface 131 is larger than 50°.

The thickness of the strap hinge 130 can be 0.7 mm to 1.5 mm and is preferably 1.1 mm so that the flexible rim 140 can be easily pulled back toward the upper and lower parts.

Hereinafter, processes of coupling the storage cover 100 and the storage case 200 according to the present invention with each other will be described.

FIG. 9 is a sectional view illustrating a state before the storage case and the storage cover according to an embodiment of the present invention are coupled with each other.

The flexible rim 140 is pulled back to the opposite side (that is, the upper part of the cover unit 110) of the storage case 200 before the storage case 200 and the storage cover 100 are coupled with each other.

When the stored goods are completely taken in the storage case 200 or are completely taken out from the storage case 200, the cover unit 110 is settled in the opening 210 of the storage case 200.

Then, when the flexible rim 140 is pulled back toward the lower part, as illustrated in FIG. 10, the flexible rim 140 surrounds the external circumference of the opening 210 of the storage case 200 to be closed.

Here, when the airtight protrusions 142a, 142b, 142c, 142d, and 142e are provided in at least one of the settling protrusions 111, the reinforcing parts 120, and the flexible rim 140, the coupling force between the storage case 200 and the storage cover 100 improves and the airtightness improves.

Figure 11:
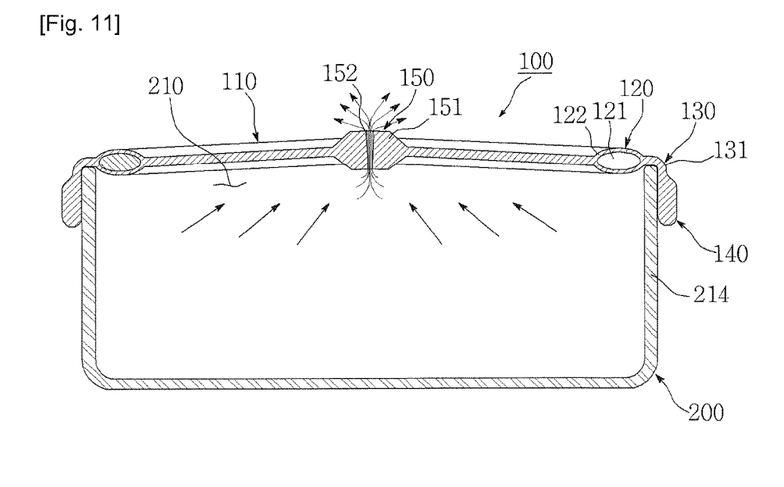
FIG. 11 is a sectional view illustrating a state where a ventilation unit is protruded by internal air or heat in the cover unit according to an embodiment of the present invention.

When the storage case 200 and the storage cover 100 are completely coupled with each other, as illustrated in FIG. 11, the center of the cover unit 110 protrudes to the opposite side of the storage case 200 due to the air pressure of the storage case 200 or the pressure of the air expanded by the heat generated by high temperature food.

Figure 12:
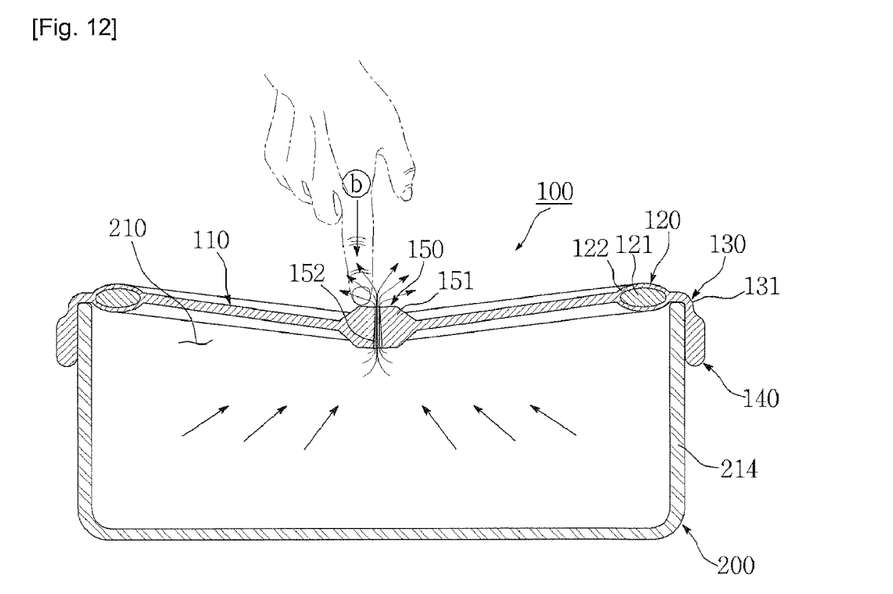
FIG. 12 is a sectional view illustrating a state where the internal air of the storage case according to an embodiment of the present invention is discharged to the outside by the pressure of a user.

At this time, when the internal air or the expanded air of the storage case 200 is to be discharged to the outside of the storage case 200, as illustrated in FIG. 12, the protrusion jaw 151 of the ventilation unit 150 is pressed toward the storage case 200 (in the direction of the arrow b).

When the protrusion jaw 151 is pressed, the center of the cover unit 110 becomes concave toward the storage case 200 so that the ventilation hole 152 is opened and that the internal air or the expanded air of the storage case 200 is discharged to the outside of the storage case 200.

After the air or the heat in the storage case 200 is discharged to the outside, when pressure toward the protrusion jaw 151 is released, the cover unit 110 is restored to the original shaped.

Figure 13:
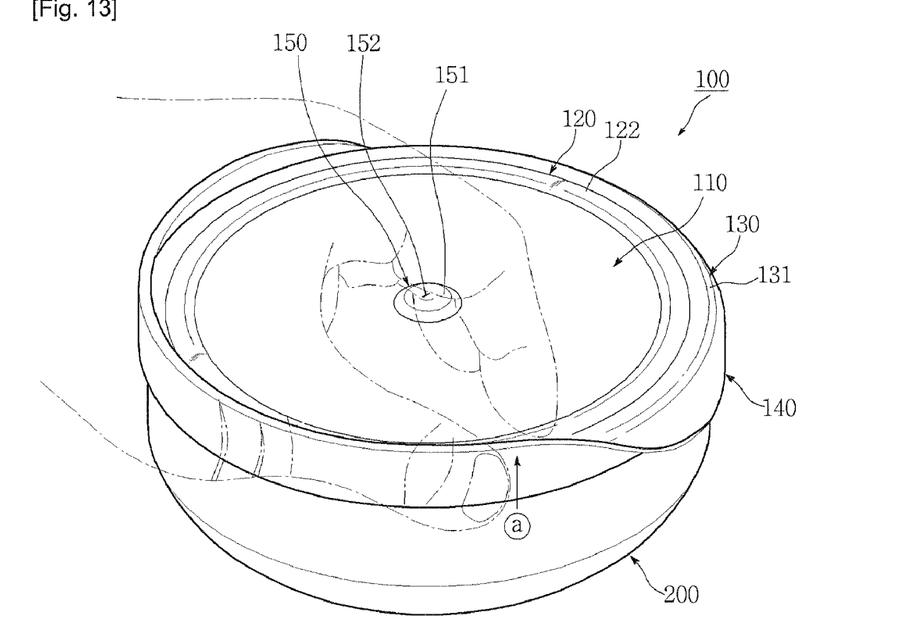
FIG. 13 is a perspective view illustrating a state where a flexible rim according to an embodiment of the present invention is pulled back.

On the other hand, in a case where the storage cover 100 is released from the storage case 200 in order to take in or out the stored goods, as illustrated in FIG. 13, when only a part of the flexible rim 140 is lifted by the fingers of a user by a one-touch method (in the direction of the arrow a), the entire flexible rim 140 is pulled back toward the upper part of the cover unit 110.

As described above, the released cover unit 110 is deviated from the opening 210 of the storage case 200 to take the stored goods in the storage case 200 or to take out the stored goods from the storage case 200.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

[Industrial Applicability]

In the storage cover for the storage case according to the present invention having the above-described structure, the opening and closing operations can be simply performed by pulling back the upper and lower parts by the one-touch method and the airtight coupling force can be maintained in spite of the repeated opening and closing operations.

In addition, when the storage cover is made of flexible rubber or synthetic resin, the storage cover is prevented from being transformed and twisted due to the reinforcing units.

In addition, when the storage cover is made of flexible silicon, the original coupling force and airtightness can be maintained although the storage cover is used for a long time.

In addition, the internal and external sides of the flexible rim integrated with the circumference of the cover unit have the same structure and function so that both surfaces of the storage cover can be used regardless of the upper and lower sides of the storage cover.

In addition, the air or heat in the storage case can be discharged to the outside in a state where the storage cover is not opened so that the freshness of the food kept in the storage case can be maintained.

The invention claimed is:

1. A storage cover for a storage case for opening and closing an opening formed on one side of a storage case to take in and out stored goods, the storage cover for the storage case comprising:
   a plate-shaped cover unit for covering the upper part of the opening; and a flexible rim extended downwards along the edge of the cover unit formed in a ring shape and made of an elastic material to be elastically extended for abutting against outer upper rim of the storage case, wherein a side of the flexible rim is pulled outwardly, parting away from the outer upper rim of the storage case, and then, upwardly such that portions of the flexible rim adjacent to the side of the flexible rim are pulled continuously upwardly, the whole flexible rim is automatically and instantly pulled up and, as a result, the cover unit is released from the storage case, wherein a side of the flexible rim is pulled outwardly and downwardly such that portions of the flexible rim adjacent to the side of the flexible rim are pulled continuously downwardly, the whole flexible rim is pulled down at once and, as a result, the cover unit closes the storage case.

2. The storage cover for the storage case as claimed in claim 1, wherein the cover unit further comprises a plurality of settling protrusions that protrude toward the storage case, and wherein the settling protrusions are separated from the flexible rim by no less than the thickness of the side walls of the storage case to guide the cover unit so that the cover unit is settled in the correct position of the opening.

3. The storage cover for the storage case as claimed in claim 2, wherein the plurality of settling protrusions are connected to each other to be ring-shaped.

4. The storage cover for the storage case as claimed in claim 2, wherein at least one airtight protrusions that protrude toward the side walls of the storage case to be connected to the side walls to improve airtightness are further formed in at least one of the settling protrusions and the flexible rim.

5. The storage cover for the storage case as claimed in claim 1, wherein the flexible rim is made of silicon having elasticity.

6. The storage cover for the storage case as claimed in claim 1, wherein the cover unit and the flexible rim are made of silicon having elasticity, and wherein reinforcing units that let the cover unit maintain the original shape when the flexible rim is pulled back are further provided in the cover unit.

7. The storage cover for the storage case as claimed in claim 6, wherein the reinforcing units comprise reinforcing rings adjacent to the edge of the cover unit to be buried in the cover unit.

8. The storage cover for the storage case as claimed in claim 7, wherein the reinforcing units are provided to protrude toward the storage case and are separated from the flexible rim by no less than the thickness of the side walls of the storage case to guide the cover unit so that the cover unit is settled in the correct position of the opening.

9. The storage cover for the storage case as claimed in claim 8, wherein at least one airtight protrusions that protrude toward the side walls of the storage case to be connected to the side walls to improve airtightness are formed in at least one of the reinforcing units and the flexible rim.

10. The storage cover for the storage case as claimed in claim 9, wherein airtight protrusion accommodating units in which the airtight protrusions are accommodated and from which the airtight protrusions are released are provided on the side walls so that the airtight protrusions are inserted into the airtight protrusion accommodating units when the opening is closed to prevent the storage case from being deviated from the storage cover.

11. The storage cover for the storage case as claimed in claim 9, wherein the airtight protrusions are wrinkled.

12. The storage cover for the storage case as claimed in claim 1, wherein the cover unit further comprises at least one ventilation units for introducing and discharging the air to the inside and outside of the storage case when the opening is closed.

13. The storage cover for the storage case as claimed in claim 12, wherein the ventilation unit comprises a ventilation hole opened when external force is applied to discharge the air in the storage case to the outside and closed when external force is removed to prevent the air from being introduced to the storage case.

14. The storage cover for the storage case as claimed in claim 1, wherein the flexible rim is provided to have a thickness no less than the thickness of a strap hinge connected to the cover unit.

15. The storage cover for the storage case as claimed in claim 3, wherein at least one airtight protrusions that protrude toward the side walls of the storage case to be connected to the side walls to improve airtightness are further formed in at least one of the settling protrusions and the flexible rim.

* * * * *